(12) United States Patent
Hara et al.

(10) Patent No.: US 6,387,910 B1
(45) Date of Patent: May 14, 2002

(54) DRUG OF IMPROVING OPTIC NERVE HEAD CIRCULATION DISORDER

(75) Inventors: Hideaki Hara, Nara; Masamitsu Shimazawa; Yasushi Iwakura, both of Hyogo; Tetsuya Sugiyama, Takatsuki, all of (JP)

(73) Assignee: Akzo Nobel N.V., Arnhem (NL)

( * ) Notice: Subject to any disclaimer, the term of this patent is extended or adjusted under 35 U.S.C. 154(b) by 0 days.

(21) Appl. No.: 09/601,231

(22) PCT Filed: Jan. 21, 1999

(86) PCT No.: PCT/JP99/00202

§ 371 Date: Oct. 2, 2000

§ 102(e) Date: Oct. 2, 2000

(87) PCT Pub. No.: WO99/38515

PCT Pub. Date: Aug. 5, 1999

(30) Foreign Application Priority Data

Jan. 29, 1998 (JP) .......................................... 10-016831
Sep. 7, 1998 (JP) .......................................... 10-252375

(51) Int. Cl.$^7$ ............................................ A61K 31/495
(52) U.S. Cl. ..................... 514/255; 514/912; 514/913
(58) Field of Search ................. 514/255, 912, 514/913

(56) References Cited

U.S. PATENT DOCUMENTS 4,663,325 A    5/1987   Ohtaka et al.

FOREIGN PATENT DOCUMENTS

| WO | WO 90/06123 | 6/1990 |
|---|---|---|
| WO | WO 93/23082 | 11/1993 |

*Primary Examiner*—Zohreh Fay
(74) *Attorney, Agent, or Firm*—William M. Blackstone

(57) ABSTRACT

A novel drug for improving the circulation in the optic nerve head, which comprises as an active ingredient Lomerizine (I):

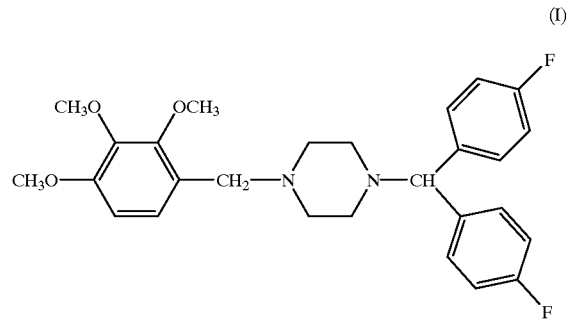

or a pharmaceutically acceptable acid addition salt. The optic nerve head circulation improving drug of this invention can increase the blood flow in the optic nerve head with no or little systemic side effects such as hypotensive activity or heart rate increasing activity and is useful particularly for the treatment of normal tension glaucoma.

18 Claims, 9 Drawing Sheets

DRUG OF IMPROVING OPTIC NERVE HEAD CIRCULATION DISORDER

FIELD OF THE INVENTION

This invention relates to a drug for the improvement of the circulation in the optic nerve head, particularly a drug for the treatment of normal tension glaucoma, which comprises as an active ingredient Lomerizine or a pharmaceutically acceptable acid addition salt thereof.

BACKGROUND OF THE INVENTION

Glaucoma is one of the main causes of blindness and is defined as "an eye disease characterized by an increase in intraocular pressure and a temporary or permanent optic nerve dysfunction due to the increase in intraocular pressure." Although this definition may be adopted to glaucoma with high intraocular pressure such as the angle-closure glaucoma or secondary glaucoma, it is not adoptable to the normal tension glaucoma without association of the increase in intraocular pressure.

Recently, attention has been given to the normal tension glaucoma which is set by optic peripheral circulation disorder such as optic nerve head circulation disorder, while the intraocular tension is within the normal range. Accordingly, various studies have been done on the syndromes thereof and for finding a method for the treatment of the disease.

On the other hand, it is known that calcium antagonists are effective for ocular circulation. The calcium antagonists can block electric potential-dependent calcium channel in the excitatory cells such as smooth muscle and cardiac muscle, inhibit flow of Ca ion into cells which induce relaxation of smooth muscle and inhibit the contraction of cardiac muscle, and thereby have widely been used for the treatment of angina pectoris and hypertension. It is also known that the actions of the calcium antagonists onto the ocular circulation are different depending on the kinds of calcium antagonists. For example, with respect to the action on the optic nerve head, Nicardipine shows week activity but Nilvadipine shows an activity of increasing blood flow in the optic nerve head (cf. "Nichi-Gan Kaishi" (Journal of Japanese Ophthalmology Society), Vol. 100, No. 12, p. 923, 1996).

Lomerizine having the following chemical formula (I) or a pharmaceutically acceptable acid addition salt thereof is a calcium antagonist having a benzylpiperazine nucleus as disclosed in JP-A-60-222472, and the dihydrochloride compound (Lomerizine hydrochloride) is now being developed as a drug for the treatment of migraine in the code name of KB 2796.

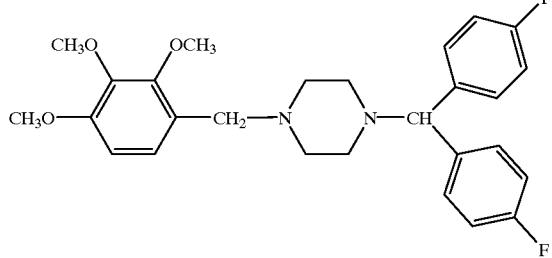

(I)

JP-A(Kohyo)-7-508030 discloses a topical ophthalmic composition for the treatment of glaucoma, which comprises a combination of a calcium antagonist and a compound having an activity of decreasing or controlling the intraocular pressure, wherein many kinds of known calcium antagonists including KB 2796 are disclosed.

It is disclosed in the above Japanese patent publication that the known calcium antagonists used in the topical ophthalmic composition for the treatment of glaucoma are "preferably those having decrease of ocular perfusion pressure and having tendency of decrease of ocular blood flow in case of lowering not so much the systemic blood pressure" (cf. the description thereof, page 4, upper right column, end line—lower left column, line 2).

However, to the contrary, Lomerizine or a pharmaceutically acceptable acid addition salt thereof does neither lower the systemic blood pressure nor decrease the ocular perfusion pressure, but can increase the ocular blood flow, as is mentioned hereinafter.

Besides, the above patent publication discloses merely the name KB 2796, but does never teach or even suggest the activity of Lomerizine or a pharmaceutically acceptable acid addition salt thereof onto the optic nerve head circulation.

SUMMARY OF THE INVENTION

It has been strongly desired to use a drug having no systemic action such as hypotensive activity for the clinical treatment of the normal tension glaucoma.

An object of this invention is to provide a novel drug for the improvement of the optic nerve head circulation, which has no systemic action such as hypotensive activity and is useful for the treatment of the normal tension is glaucoma.

The present inventors have intensively studied and found that among the many kinds of calcium antagonists, Lomerizine or a pharmaceutically acceptable acid addition salt thereof shows little hypotensive activity, that is, has weak peripheral vasodilating activity and does not increase the peripheral blood flow, but can surprisingly increase the blood flow in the ocular periphery (the optic nerve head), and then have completed this invention.

BRIEF DESCRIPTION OF DRAWINGS

In FIGS. 1, 2, 6, 7, 8 and 9, the standard errors in each data are as follows:

Figure 1:
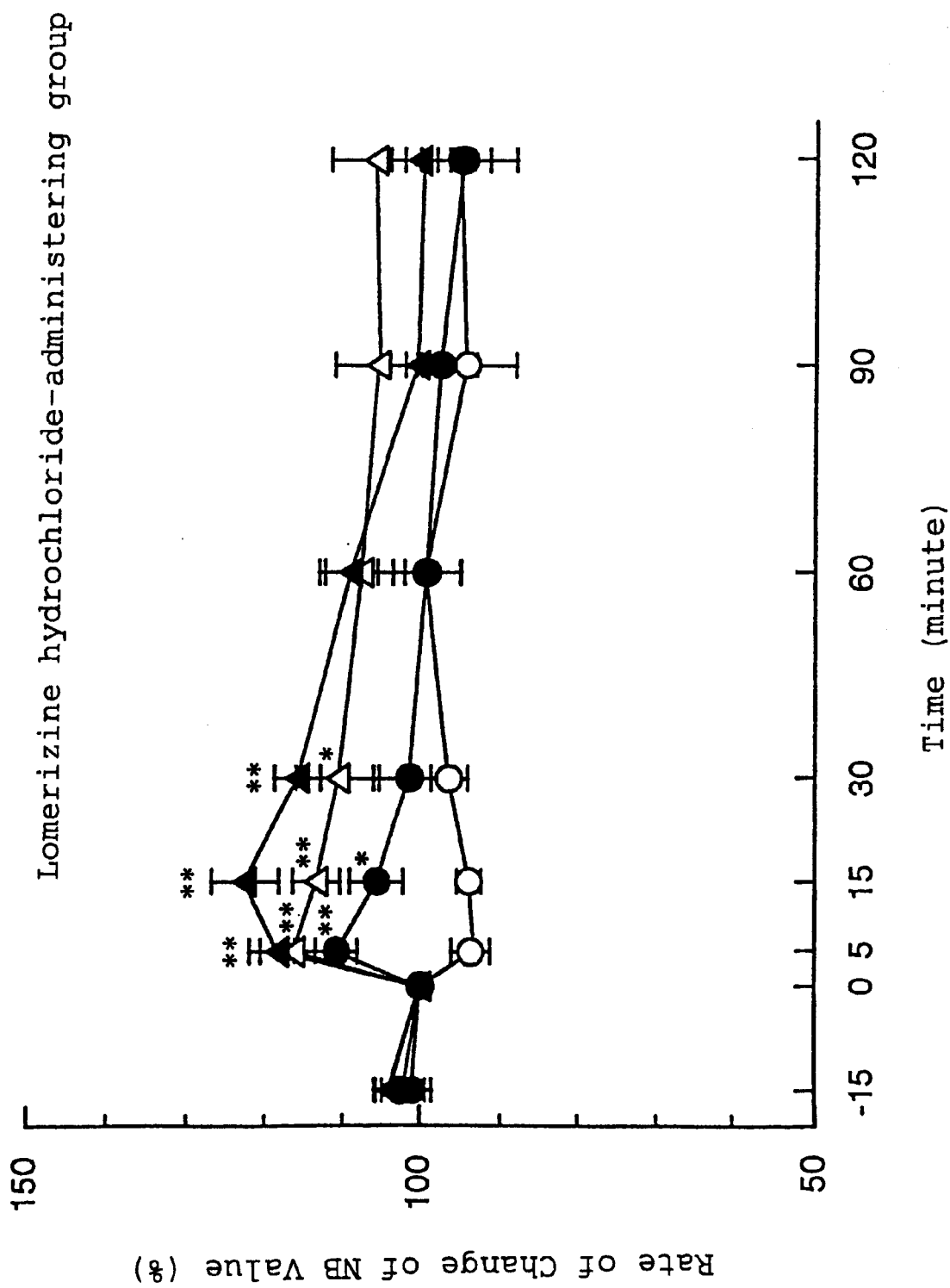
FIG. 1 shows the rate of change in NB values (normalized blur values: Blurring's quantitative index) in the group administered with Lomerizine hydrochloride in Experiment 1.

*: $p<0.05$, **: $p<0.01$ (to the vehicle-administered group)

In FIGS. 1, 3, 5, 7 and 9, each curve means as follows.

○: Vehicle-administered group

●: Lomerizine hydrochloride-administered group, 0.03 mg/kg, i.v.

△: Lomerizine hydrochloride-administered group, 0.1 mg/kg, i.v.

▲: Lomerizine hydrochloride-administered group, 0.3 mg/kg, i.v.

Besides, in FIGS. 2, 4, 6 and 8, each curve means as follows.

○: Vehicle-administered group

●: Nilvadipine-administered group, 0.003 mg/kg, i.v.

△: Nilvadipine-administered group, 0.01 mg/kg, i.v.

▲: Nilvadipine-administered group, 0.03 mg/kg, i.v.

DETAILED DESCRIPTION OF THE INVENTION

The drug for improving the optic nerve head circulation of this invention comprises as an active ingredient Lomerizine or a pharmaceutically acceptable acid addition salt thereof. These compounds are prepared by a process as disclosed, for example, in the above-mentioned JP-A-60-222472.

The pharmaceutically acceptable acid addition salt includes a salt with an inorganic acid such as hydrochloric acid, hydrobromic acid, sulfuric acid, or a salt with an organic acid such as maleic acid, fumaric acid, succinic acid, citric acid, and particularly preferable salt is dihydrochloride salt.

Besides, it is known that the pharmaceutically acceptable acid addition salt of Lomerizine is present also as in the form of polymorph or of a hydrate, and the active ingredient in the present invention includes also those polymorph or hydrate.

The drug for the improvement of the optic nerve head circulation of this invention can be administered to the patients suffering from the normal tension glaucoma in the form of a preparation suitable for oral administration or for injection, preferably in the preparation for oral administration.

The preparation for oral administration includes tablets, granules, fine granules, powders, etc. and these preparations can be prepared by conventional methods by admixing Lomerizine or a pharmaceutically acceptable acid addition salt thereof with conventional pharmaceutically acceptable additives such as lactose, corn starch, crystalline cellulose, magnesium stearate, carboxymethyl-cellulose calcium, hydroxypropyl cellulose, talc, and the like.

The preparation for injection can be prepared by dissolving Lomerizine or a pharmaceutically acceptable acid addition salt thereof in a distilled water for injection, which may optionally be incorporated with isotonic agents (e.g. mannitol, sodium chloride, glucose, sorbitol, glycerol, xylitol, fructose, maltose, mannose, etc.), stabilizers (e.g. sodium sulphite, albumin, etc.), preservatives (e.g. benzyl alcohol, methyl p-hydroxy-benzoate, etc.). The preparation may also optionally be incorporated with a pH adjusting agent such as an acid (e.g. hydrochloric acid, methanesulfonic acid, citric acid, etc.) or a base (e.g. sodium hydroxide, diisopropanolamine, etc.).

The injection preparation may be in the form of a lyophilized preparation which is dissolved in a solvent when used. The lyophilized preparation can be prepared by lyophilizing an aqueous solution of the above active ingredient, and may optionally be incorporated with the above-mentioned isotonic agents, stabilizers, preservatives, pH adjusting agents, and the like.

The drug of this invention can increase the blood flow in the optic nerve head and can improve the optic nerve head circulation, and hence is useful particularly for the treatment of the normal tension glaucoma.

The dose of the optic nerve head circulation improving drug of this invention may vary depending on the administration routes, the severity of diseases, age, weight of patients, and the like, but is usually in the range of 0.1 mg to 100 mg as Lomerizine or a pharmaceutically acceptable acid addition salt thereof, which is administered one to three times per day.

Among the above, in case of a optic nerve head circulation improving drug comprising as an active ingredient Lomerizine hydrochloride, it is particularly preferable to administer by oral route, where the dose thereof may vary depending on the severity of diseases, age and weight of the patients, but may usually be in the range of 1 mg to 40 mg as Lomerizine hydrochloride which is administered one to three times per day. Preferably it is administered at a dose of 2 mg to 10 mg, twice or three times per day.

Lomerizine or a pharmaceutically acceptable acid addition salt thereof can increase the blood flow in the optic nerve head with little systemic side effects such as hypotensive activity or increase of heart rate (cf. Experiment 1). The optic nerve head circulation improving drug of this invention has also less manifestation of other side effects (objective and subjective symptoms). Moreover, the side effect-manifestation in aged persons (65–85 years old) is not so different from that in younger persons (15–64 years old).

Accordingly, the optic nerve head circulation improving drug of this invention has high safety and can safely be used even in an aged patient, particularly for the treatment of the normal tension glaucoma.

Besides, the optic nerve head circulation improving drug of this invention is effective by oral administration (cf. Experiment 2).

The above excellent effects of the optic nerve head circulation improving drug of this invention could be confirmed by the following experiments.

That is, Lomerizine hydrochloride 20 mg (5 mg×4 tablets) was administered to healthy male volunteers (6 men) with normal intraocular pressure, and the blood flow in the central retinal artery and ophthalmic artery were measured by a ultrasonic color Doppler's method at 1.5, 3.0, 4.5 and 6.0 hours after administration of the drug. Simultaneously, the blood pressure, heart rate and intraocular pressure were also measured.

As a result, Lomerizine hydrochloride could significantly increase the blood flow in the central retinal artery at a dose which did not affect on the blood pressure and intraocular pressure. Since the central retinal artery is correlative with blood flow in the retina and the optic nerve head, it is considered that Lomerizine hydrochloride is effective for the improvement of circulation dysfunction in the retina and in the optic nerve head at a dose at which it does not affect on the blood pressure and the intraocular pressure. Besides, Lomerizine hydrochloride showed no significant action on the blood flow in the ophthalmic artery. Further, four and half hours after administration, it showed a temporary lowering of the heart rate.

When the effects of Lomerizine hydrochloride on the blood flow lowering in the optic nerve head induced by administration of Endothelin-1 was observed by the method of Sugiyama et al. [cf. Tetsuya SUGIYAMA and Ikuo AZUMA, "Atarashii Ganka" (Journal of the Eye), Vol. 14, No. 5, pp. 745–748, 1997]. As a result, it showed dose-dependent inhibition of lowering of blood flow in the optic nerve head (cf. Experiment 3).

Moreover, it is expected from the following experimental results that the optic nerve head circulation improving drug of this invention can inhibit the death of neurocytes in retina which is usually observed in patients suffering from glaucoma.

That is, in view of the facts that within the vitreous body of glaucoma patients glutamic acid is contained in so high concentration as to induce death of neurocyte and that the neurocytes in retina disappear by exposing to glutamic acid in experimental models, the following experiments have been done.

From an embryo of a pregnant rat (18th days after confirmation), the neurocytes in retina were isolated and cultivated for 10 days, and were treated with glutamic acid (500 μM) for 10 minutes. The resultant was incubated in a medium containing no glutamic acid for one hour, and then was subjected to examine the neurotoxicity with glutamic acid by a Trypan blue-exclusion method. Lomerizine hydrochloride was applied to the neurocytes to be tested from 30 minutes prior to the treatment with glutamic acid till one hour after the evaluation of the survival rate of the cells.

As a result, Lomerizine hydrochloride showed dose-dependently inhibitory activity against the death of neurocytes induced by glutamic acid, and showed significant inhibitory activity in an amount of 0.01, 0.1 and 1 μM.

The effects of the present drug are illustrated by the following Examples.

EXAMPLE 1

The Optic Nerve Head Circulation Improving Activity

The optic nerve head circulation improving activity was measured by using as an index the rate of change of NB value as mentioned hereinafter.
(1) Test Compounds:
  Lomerizine hydrochloride
  Nilvadipine (Positive control)
(2) Test Method:
  1) Measurement of Blood Flow in the Optic Nerve Head by Laser Speckle Technique Male New Zealand White rabbits (weighing 2.3–3.1 kg) were housed in an OSHIDA-type solid box and the left auricula was locally anesthetized with Xylocaine Spray (trademark, manufactured by Fujisawa Pharmaceutical) and Xylocaine Jelly (trademark, manufactured by Fujisawa Pharmaceutical), and a catheter (Polyethylene Tube SP28, manufactured by Natsume) were inserted into the post auricular artery for measuring the blood pressure and the heart rate, and the blood pressure and the heart rate were continuously recorded with a recorder (WT-645G, manufactured by Nihon-Koden). Under the local anesthesia, a catheter for administering the test drug (Polyethylene Tube SP31, manufactured by Natsume) was likewise inserted into the right post auricular vein of the animal. The animals were led to mydriasis at both eyes by dropping Mydrin M (trademark, manufactured by Santen Pharmaceutical), and then the right eye was locally anesthetized by dropping a 0.4% solution of Benoxil (trademark, manufactured by Santen Pharmaceutical), and control threads were hung onto the superior rectus muscle and the inferior rectus muscle.

The blood flow of the optic nerve head was measured by selecting a portion having no surface blood vessel at the right optic nerve head [0.42×0.42 mm (field angle 30°) with an eyegrounds circulation analyzer (Laser speckle circulation analyzer-II: LSCA-II), measuring the mean value of the quantitative index of blurring in whole field (100×100) [NB value (normalized blur value)], and calculating the rate of change (%) of the NB value by the following equation:

$$\text{Rate of Change of } NB \text{ value } (\%) = \frac{NB \text{ value after administration of drug or vehicle}^*}{NB \text{ value before administration of drug or vehicle}} \times 100$$

*) The NB value after administration of drug or vehicle was measured by administering the test drug or the vehicle (as a control) in a volume of 0.1 ml/kg over a period of one minute intravenously (i.v.) respectively and then measuring the value at 5, 15, 30, 60, 90 and 120 minutes after the administration By the way, the test drug was prepared by adding a 20% dimethylacetamide solution containing 2% tartaric acid to a drug to be tested so as to adjust the ad ministration volume thereof to 0.1 ml/kg and dissolving the mixture by adding thereto a hot water.
  2) Measurement of Intraocular Pressure The intraocular pressure was measured on the left eye at each time when the above NB values were measured after the administration of drug or vehicle (excepting 5 minutes after administration, the intraocular pressure was not measured) after dropping a 0.4% solution of Benoxil (trademark, manufactured by Santen Pharmaceutical) by using a calibrated pneumatonometer (Alcon Application Pneumatonograph, manufactured by Nippon Alcon).
  3) Statistics The change of the value between the data after administration of drug or vehicle and the data before the administration of drug or vehicle was determined, and for each item, the mean values and standard deviation in six animals in each test were determined, and the results are shown in the accompanying FIG. 1 to FIG. 8. The significant test of the test drug was done by t-test at each time of measurement compared to the data in the control group administered with vehicle. The significant standards are indicated separately in the group of less than 5% and the group of less than 1%.
(3) Test Results In the groups administered with Lomerizine hydrochloride (0.03, 0.1 and 0.3 mg/kg, i.v.), the blood flow in the optic nerve head was increased in comparison with that in the groups administered with the vehicle. At each time of the measurement, Lomerizine hydrochloride was effective for increasing dose-dependently the blood flow at the optic nerve head and showed significant difference 5 and 15 minutes after administration in comparison with the groups administered with vehicle. Besides, in the groups administered with 0.1 or 0.3 mg/kg of Lomerizine hydrochloride, it showed significant increasing effects even 30 minutes after administration (cf. FIG. 1). On the other hand, at the same dosage, the groups administered with Lomerizine hydrochloride showed no significant action on the intraocular pressure, mean blood pressure and heart rate in comparison with the groups administered with vehicle except that in the group administered with 0.3 mg/kg of the drug, a certain significant increase in the heart rate was observed 5 minutes after the administration (cf. FIGS. 3, 5 and 7).

In the groups administered with Nilvadipine (0.003, 0.01 and 0.03 mg/kg, i.v.), there was also observed higher increasing activity of blood flow in the optic nerve head in comparison with the groups administered with vehicle and it was significant 5 minutes after the administration.

Figure 2:
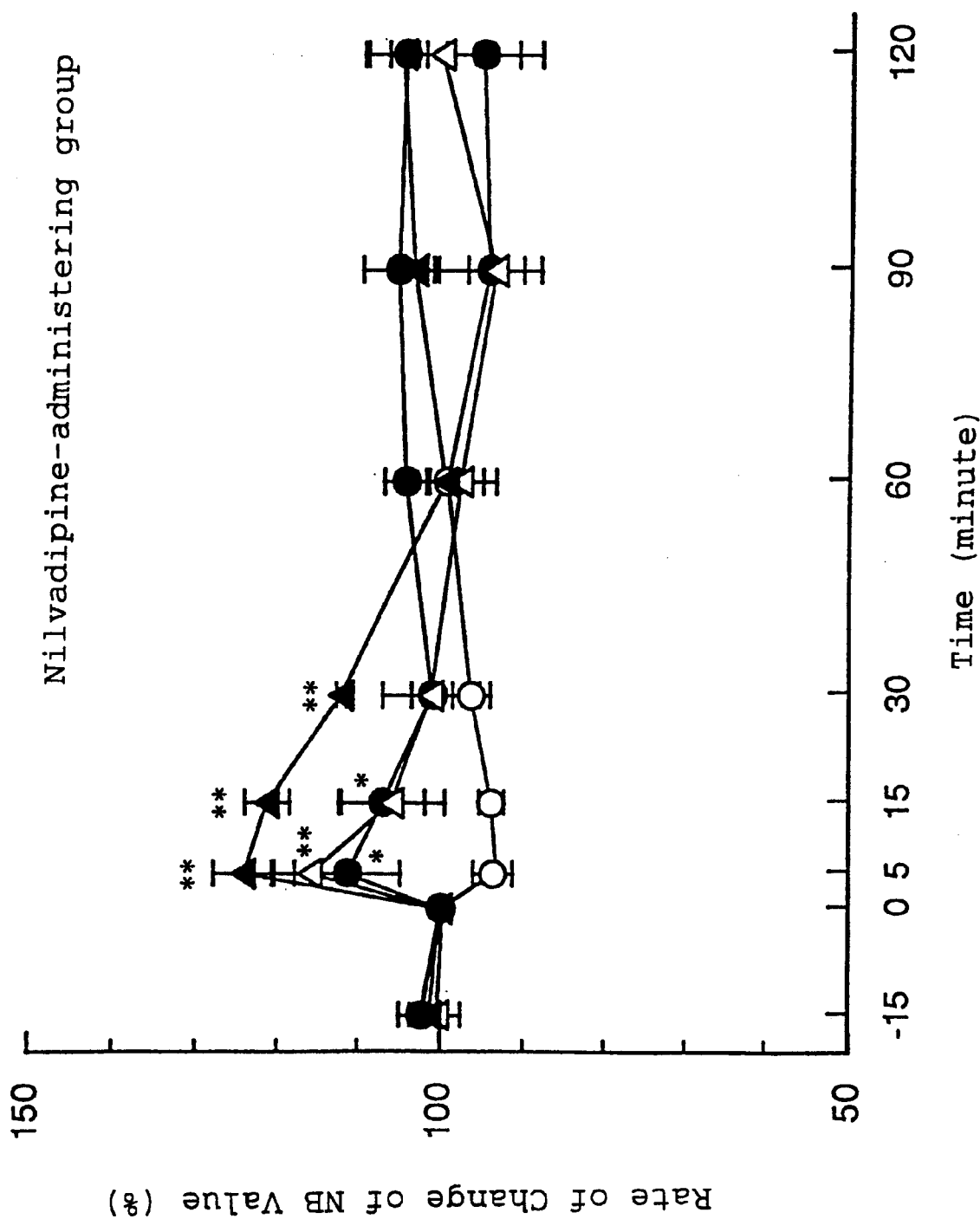
FIG. 2 shows the rate of change in NB values in the Nilvadipine-administered group in Experiment 1.
Figure 3:
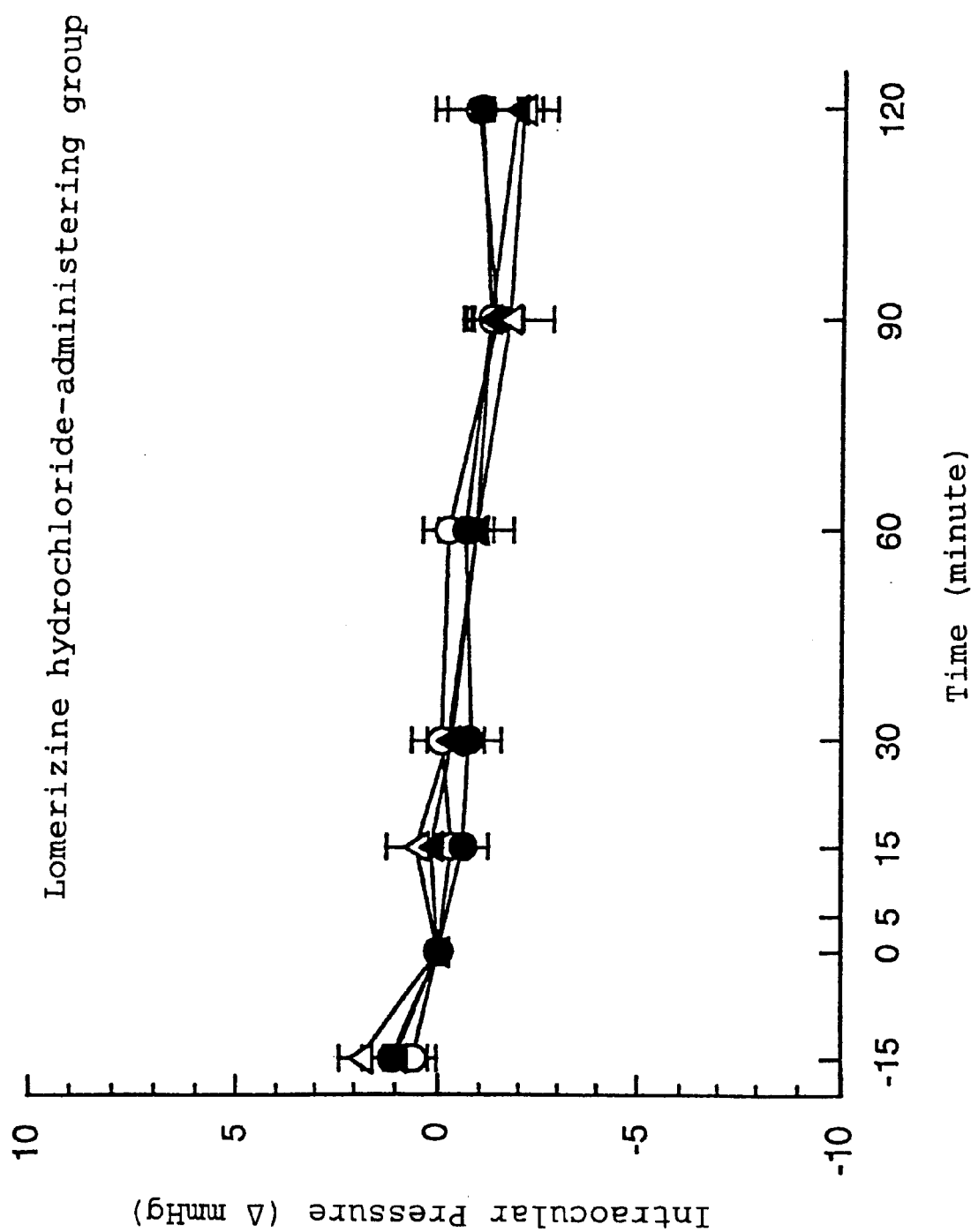
FIG. 3 shows the intraocular pressure in the Lomerizine hydrochloride-administered group in Experiment 1.
Figure 4:
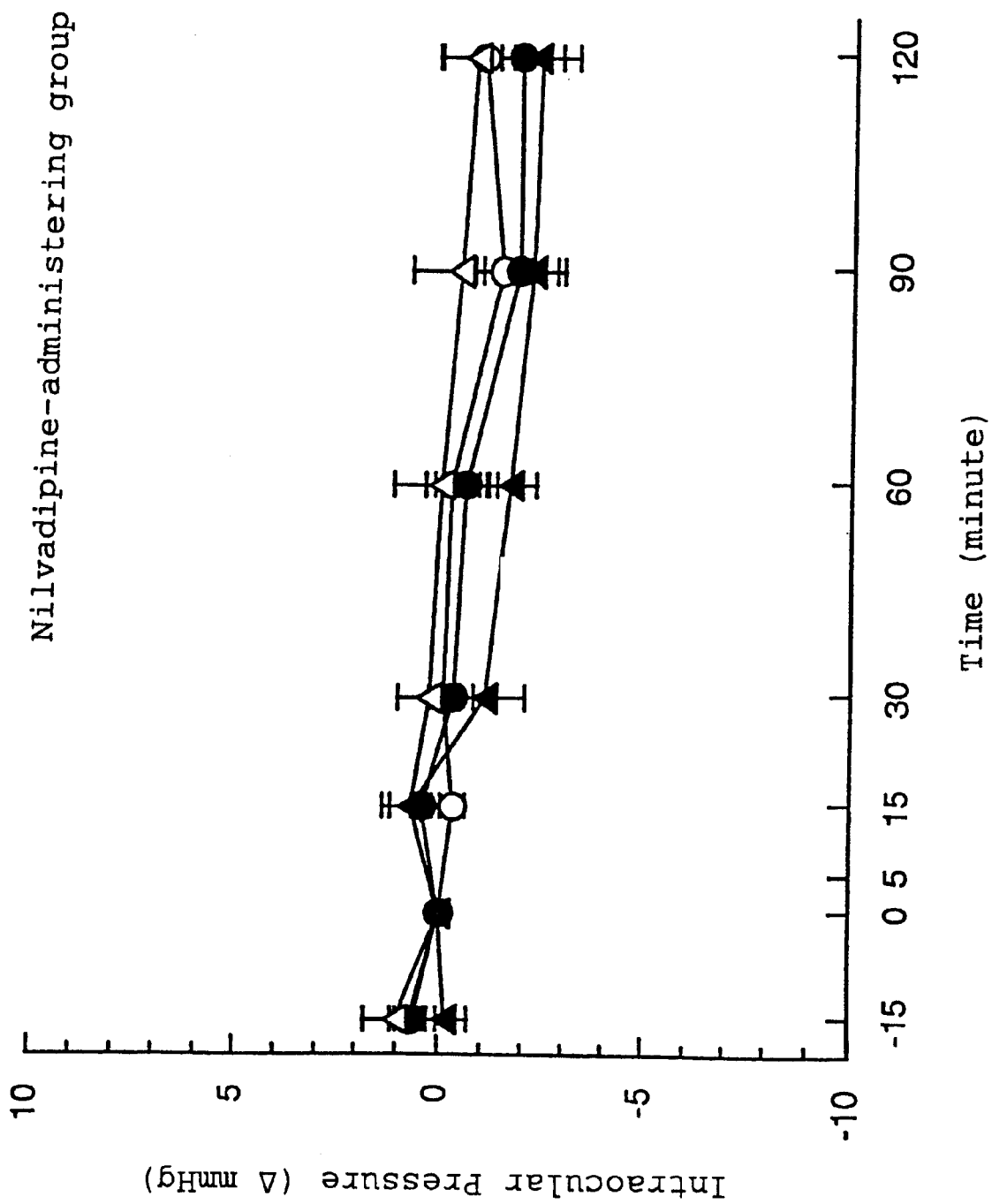
FIG. 4 shows the intraocular pressure in the Nilvadipine-administered group in Experiment 1.
Figure 5:
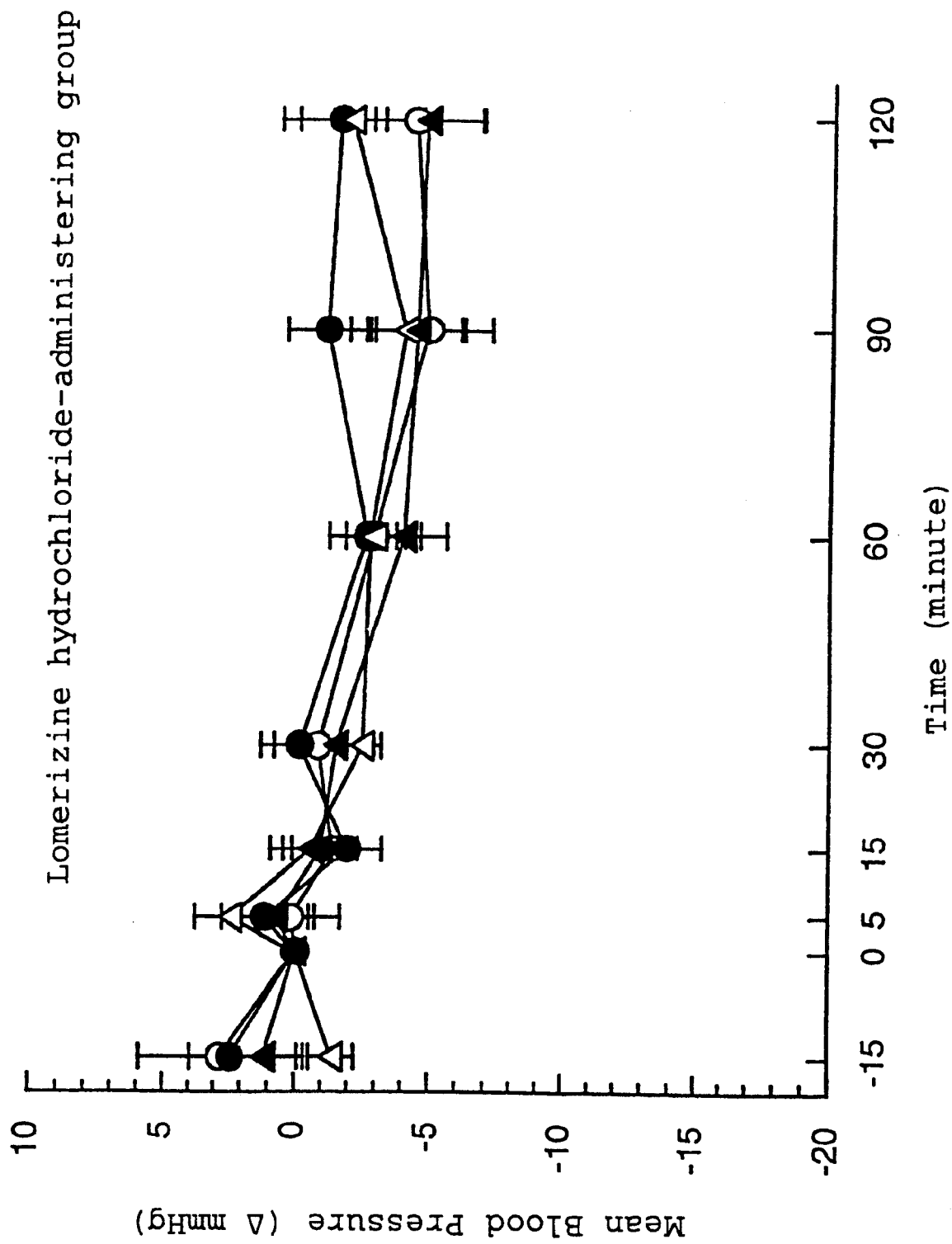
FIG. 5 shows the mean blood pressure in the Lomerizine hydrochloride-administered group in Experiment 1.
Figure 6:
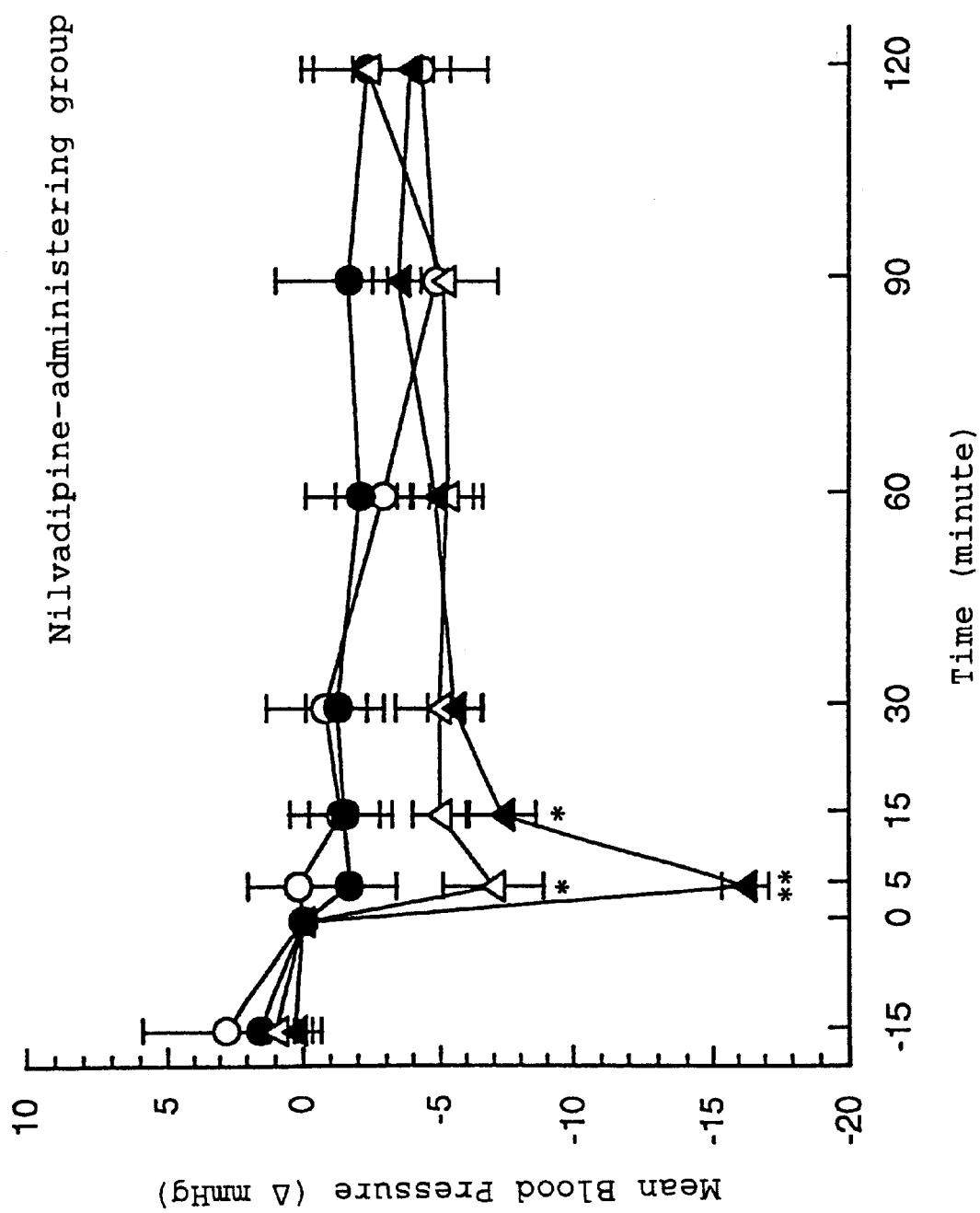
FIG. 6 shows the mean blood pressure in the Nilvadipine-administered group in Experiment 1.
Figure 7:
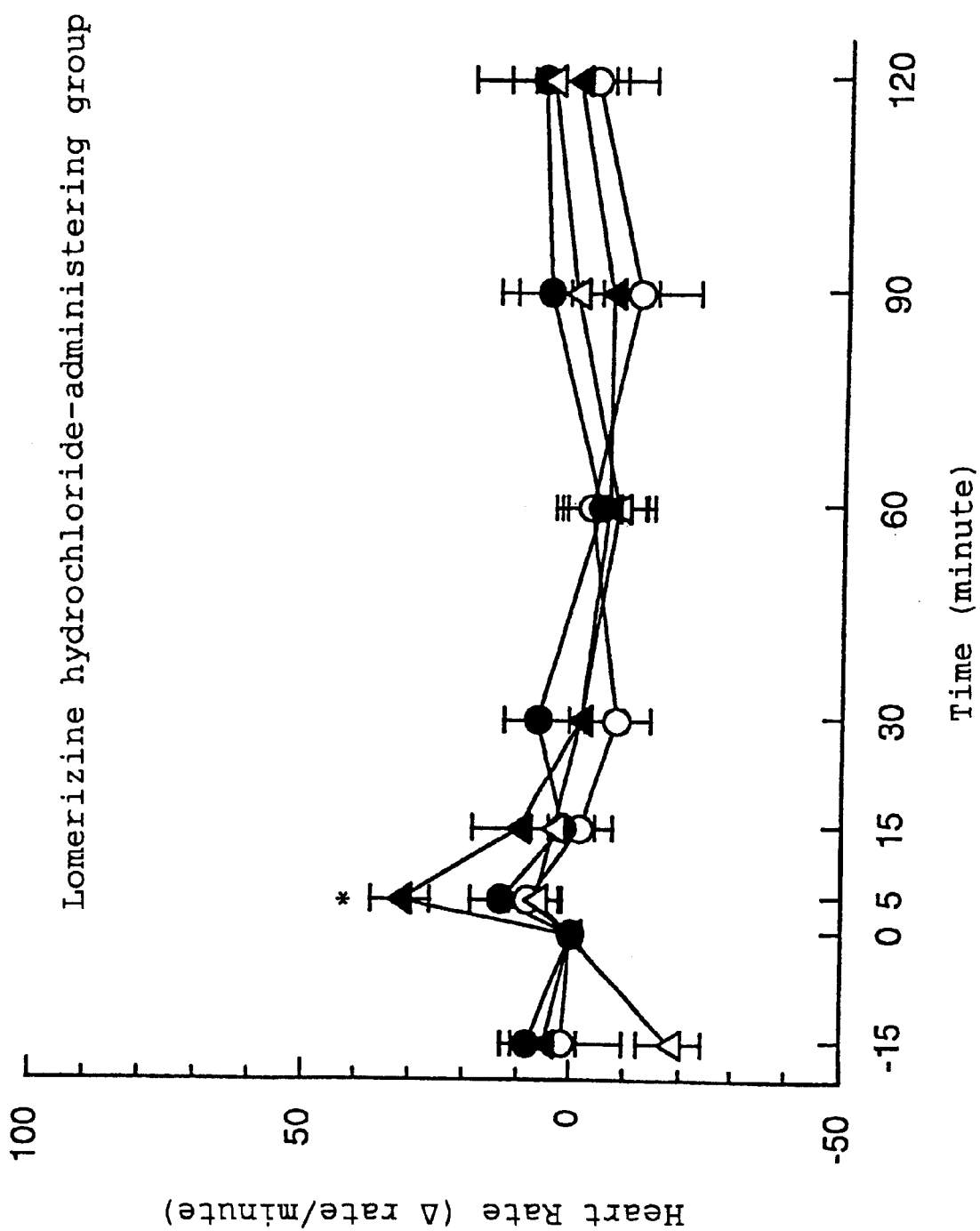
FIG. 7 shows the heart rate in the Lomerizine hydrochloride-administered group in Experiment 1.
Figure 8:
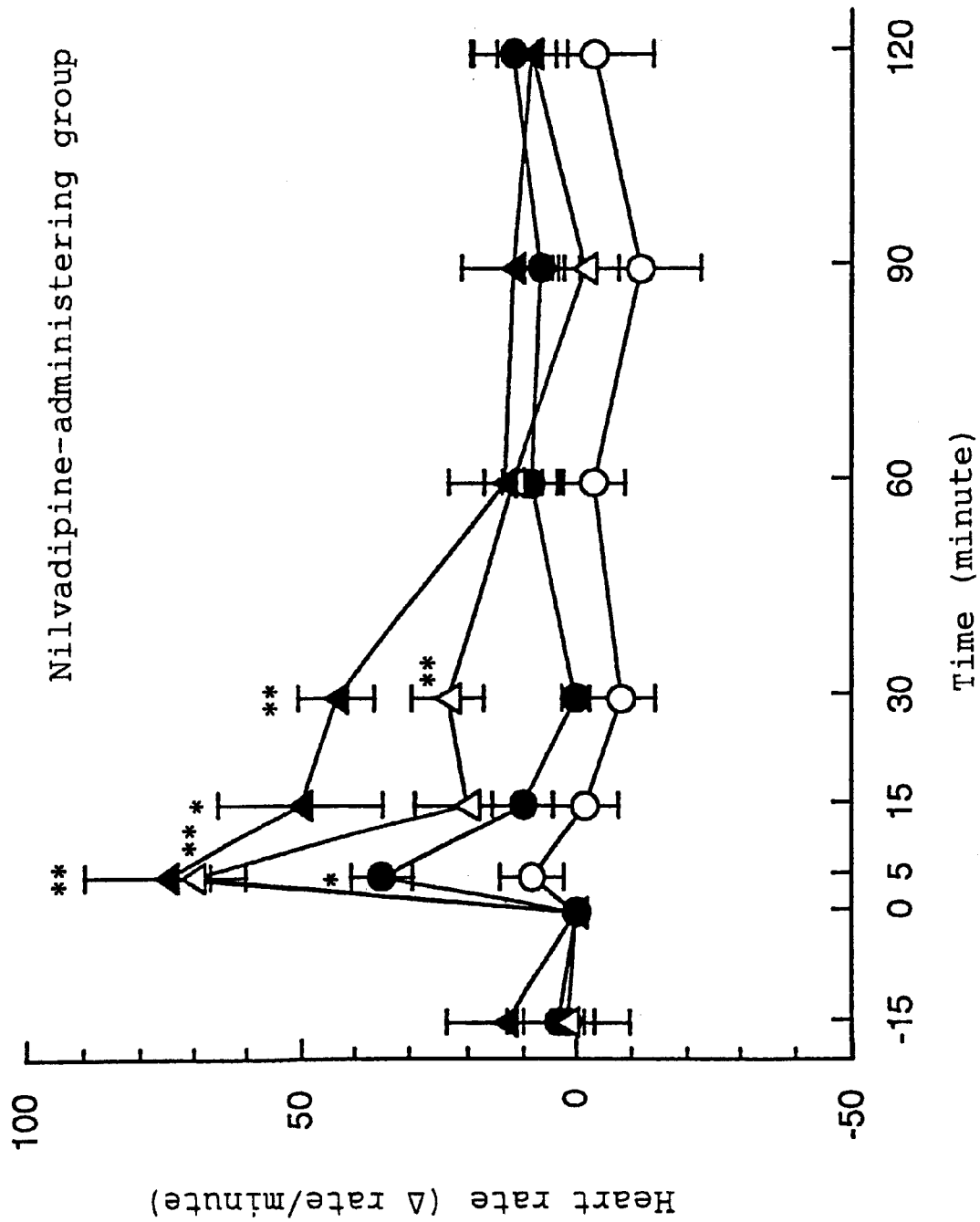
FIG. 8 shows the heart rate in the Nilvadipine-administered group in Experiment 1.

Furthermore, significant increasing activity was observed in the groups administered with 0.003 and 0.03 mg/kg of drug 15 minutes after the administration and in the groups administered with 0.03 mg/kg of drug 30 minutes after the administration (cf. FIG. 2). However, significant hypotensive activity was observed in the groups administered with 0.01 and 0.03 mg/kg of drug 5 minutes after the administration and in the groups administered with 0.03 mg/kg of drug 15 minutes after the administration (cf. FIG. 6). Besides, significant increase in the heart rate was observed in all groups 5 minutes after the administration, in the groups administered with 0.03 mg/kg of drug 15 minutes after the administration and in the groups administered with 0.01 and 0.03 mg/kg of drug 30 minutes after the administration (cf. FIG. 8). On the other hand, in the groups administered with Nilvadipine, no clear action on the intraocular pressure was observed (cf, FIG. 4).

As is clear from the above results, Nilvadipine showed dose-dependently hypotensive activity and heart rate increasing activity along with the activity of increasing the blood flow in the optic nerve head, but on the contrary, Lomerizine hydrochloride could increase the blood flow in the optic nerve head with no or much less systemic side effects such as hypotensive activity or heart rate increasing activity and hence it has high safety and will be able to use even to aged patients with high safety.

EXAMPLE 2

Measurement of Plasma Concentration of Drug in Rabbit

Under the same conditions as in the above Example 1, the plasma concentration of Lomerizine in the groups administered with Lomerizine hydrochloride (0.03 mg/kg, i.v.) 5, 15, 30 and 60 minutes after the administration of the drug as follows.
(1) Test Compounds:
  Lomerizine hydrochloride
(2) Test Method:
  Male New Zealand White rabbits (weighing 2.5–3.5 kg, 3 animals per group) were placed in an OSHIDA-type solid box. A solution of Lomerizine hydrochloride (in an amount so as to be 0.03 mg/kg) in a 20% dimethylacetamide containing 2% tartaric acid was prepared and was administered to the right post auricular vein of the animals. Thereafter, blood sampling was done from left post auricular vein 5, 15, 30 and 60 minutes after the administration of test drug. The collected blood sample was centrifuged (4° C., 3000 rpm×10 minutes) to obtain a plasma sample, and then the amount of Lomerizine in the plasma was measured by gas chromatography.

The gas chromatography was carried out under the following conditions:
Machines to be Used:
  GC-14B type gas chromatograph (manufactured by Shimadzu Corporation)
  FTD Detector (Shimadzu FTD-8, manufactured by Shimadzu Corporation)
Conditions for Measurement:
  Column: Shimadzu CBP1-M25-025 (25m×0.2mm, thickness of membrane: 0.25 μm)
  Injection port temperature: 310° C.
  Column temperature: 285° C.
  Detector temperature: 310° C.
  Carrier gas: Helium (2.30 kg/m²)
  Make up gas: Helium (flow rate: 40 ml/minute)
  $H_2$ flow rate: 3.8 ml/minute
  Air flow rate: 160 ml/minute
(3) Test Results:
  The results are shown in Table 1.

TABLE 1

| Concentration of Lomerizine in Plasma | |
|---|---|
| Time for measurement (minute) | Mean ± Standard deviation (ng/ml) |
| 5 | 19.8 ± 6.5 |
| 15 | 8.1 ± 2.4 |
| 30 | 4.9 ± 2.4 |
| 60 | N.D. |

N.D.: Detection limit (2 ng/ml)

In view of the above test results as well as the data shown in a literature that when Lomerizine hydrochloride was administered to healthy male volunteers in an amount of 10 mg, 20 mg or 40 mg by oral administration, the plasma levels of Lomerizine (maximal plasma level) were 7.3±2.9, 15.7±6.4, or 31.3±10.5 (ng/ml), respectively [cf. "Yakuri-to-Chiryo" (Japanese Pharmacology and Therapeutics), Vol. 22 (11), pp. 167–172, 1994], it will be assumed that the above effects of increase of blood flow in the optic nerve head of Lomerizine hydrochloride with no or less systemic side effects such as hypotensive activity and heart rate increasing activity as found in Example 1 would also be observed by oral administration in human beings.

EXAMPLE 3

Action Against Blood Flow Decrease in the Optic Nerve Head Induced by Endothelin (1) Test Compound:
  Lomerizine hydrochloride
(2) Test Method:
  1) Measurement of Blood Flow in the Optic Nerve Head by a Hydrogen Gas Clearance Method
  Male New Zealand White rabbits (weighing 2.7–3.7 kg) were fixed on a warm pad under anesthetizing with halothane (1.5–2%), and a catheter for administering the test drug (Polyethylene Tube SP31, manufactured by Natsume) was inserted into the left femoral vein of the animal. The animals were led to mydriasis at right eye by dropping Mydrin M (trademark, manufactured by Santen Pharmaceuticals), and then the eye was anesthetized by dropping a 0.4% solution of Benoxil (trademark, manufactured by Santen Pharmaceutical), and the upper eyelid was hung up with a thread. After cut opening the conjunctiva, the exposed inferior rectus muscle was threaded to fix the eye. A needle electrode (a needle type hydrogen electrode, manufactured by M. T. Giken) was inserted into the vitreous body through the ciliary flat portion (at the side of the posterior pole of lens in 3 mm distance from the ring portion) and it was pierced in about 0.6 mm in depth into the optic nerve head under observing with a microscope with a vitrectomy lens (a plane lens for operation of vitreous body, manufactured by Kyoto Contact Lens) with taking care of not injuring blood vessel. Under anesthetizing with halothane, the animals were inhaled with hydrogen gas with an inhalation mask in a flow rate of 0.2 liter/min for 4 minutes, and then the inhalation was stopped. Based on the clearance curve of hydrogen concentration, the half-life period was calculated by a computer to determine the blood flow rate in the tissue, and then the rate of change (%) of the blood flow was calculated by the following equation:

Rate of Change of blood flow (%) =
$$\frac{\text{Blood flow after administration of drug or vehicle}^*}{\text{Blood flow before administration of drug or vehicle}} \times 100$$

*) The blood flow after administration of drug or vehicle was measured by administering the test drug or the vehicle (as a control) in a volume of 0.1 ml/kg over a period of one minute into the femoral vein (i.v.) after 5 minutes therefrom administering endothelin-1 (manufactured by Peptide Institute, $10^{-6}$M $100 \mu l$) into the vitreous body, and then measuring it at 15, 45, 75, 105, 135 and 165 minutes after the administration of endothelin-1.

The $10^{-6}$M solution of endothelin-1 was prepared by dissolving in 0.1% acetic acid in a concentration of $10^{-4}$M and diluting the mixture with an artificial ophthalmic perfusing liquid Opeguard MA (trademark, manufactured by Senju Pharmaceutical).

By the way, the test drug was prepared by adding a 20% dimethylacetamide solution containing 2% tartaric acid to a drug to be tested so as to adjust the administration volume thereof to 0.1 ml/kg and dissolving the mixture by adding thereto a hot water.

2) Statistics

Figure 9:
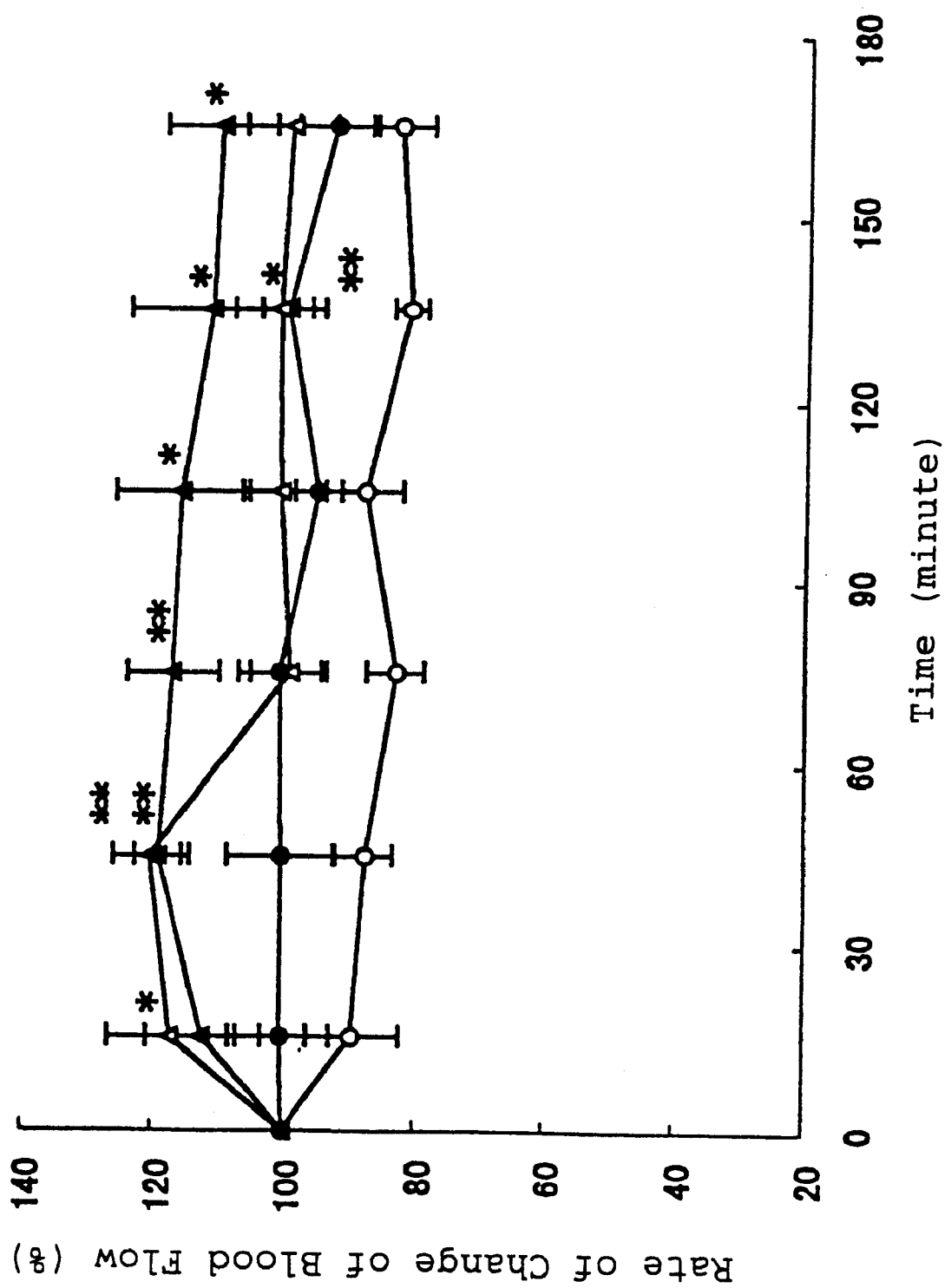
FIG. 9 shows the rate of change in blood flow in the Lomerizine hydrochloride-administered group in Experiment 3.

The mean values of blood flow and standard errors in each six animals were determined, and the results are shown in the accompanying FIG. 9. The significant test of the test drug was done by t-test at each time of measurement compared to the data in the control group administered with vehicle. The significant standard are indicated separately in the group of less than 5% and the group of less than 1%.

(3) Test Results

In the groups administered with Lomerizine hydrochloride (0.03, 0.1 and 0.3 mg/kg, i.v.), the lowering of the blood flow in the optic nerve head due to endothelin-1 was inhibited dose-dependently, and there was observed significant difference in the group administered 0.03 mg/kg of the drug at 135 minutes after the administration in comparison with that in the groups administered with the vehicle. Besides, significant inhibition was observed in the group administered with 0.1 mg/kg of the drug at 15, 45 and 135 minutes after administration, and in the group administered with 0.3 mg/kg of the drug at 45, 75, 105, 135 and 165 minutes after administration of the drug (cf. FIG. 9).

EXAMPLE 4

Tablets

Lomerizine hydrochloride (5 parts by weight), lactose (30 parts by weight) and crystalline cellulose (33 parts by weight) were homogeneously mixed, and to the powdery mixture was added a 5% aqueous solution of corn starch (7.5 parts by weight), and the mixture was granulated by a wet granulation method. The granules thus obtained were mixed with corn-starch (22.5 parts by weight) and magnesium stearate (2 parts by weight), and the mixture was tableted to give tablets (1 tablet: 100 mg containing 5 mg of Lomerizine hydrochloride).

EXAMPLE 5

Granules

Lomerizine hydrochloride (5 parts by weight) and lactose (50 parts by weight) were homogeneously mixed, and to the powdery mixture was added a 5% aqueous solution of corn starch (45 parts by weight), and the mixture was granulated by a wet granulation method to give granules containing 5 mg of Lomerizine hydrochloride per 100 mg.

Industrial Application

The Lomerizine or a pharmaceutically acceptable acid addition salt thereof contained as an active ingredient in the optic nerve head circulation improving drug of this invention can increase the blood flow in the optic nerve head with almost no systemic side effects such as hypotensive activity or heart rate increasing activity and with less manifestation of other side effects (subjective symptoms or objective symptoms) and it has further characteristics that the side effect-manifestation in aged persons (65–85 years old) is not so different from that in younger persons (15–64 years old), and hence, the drug of this invention is useful for improving the circulation in the optic nerve head, particularly for the treatment of the normal tension glaucoma.

What is claimed is:

1. A method for improving the circulation in the optic nerve head, which comprises administering orally an effective amount of Lomerizine or a pharmaceutically acceptable acid addition salt thereof to a subject in need thereof.

2. The method of claim 1, wherein the subject is suffering from an optic neuropathy.

3. The method of claim 1, wherein the subject is a human.

4. The method of claim 2, wherein the subject is a human.

5. The method of claim 4, wherein the optic neuropathy is glaucoma.

6. The method of claim 4, wherein the optic neuropathy is normal tension glaucoma.

7. A method for improving the circulation in the optic nerve head, which comprises injecting an effective amount of Lomerizine or a pharmaceutically acceptable acid addition salt thereof to a subject in need thereof.

8. The method of claim 7, wherein the subject is suffering from an optic neuropathy.

9. The method of claim 7, wherein the subject is a human.

10. The method of claim 8, wherein the subject is a human.

11. The method of claim 10, wherein the optic neuropathy is glaucoma.

12. The method of claim 10, wherein the optic neuropathy is normal tension glaucoma.

13. The method of claim 7, wherein the Lomerizine or a pharmaceutically acceptable acid addition salt thereof is administered intravenously.

14. A method for treating normal tension glaucoma, comprising the step of administering orally an effective amount of Lomerizine or a pharmaceutically acceptable acid addition salt thereof to a patient suffering from normal tension glaucoma.

15. The method of claim 14, wherein the pharmaceutically acceptable acid addition salt is dihydrochloride.

16. A method for treating normal tension glaucoma, comprising the step of injecting an effective amount of Lomerizine or a pharmaceutically acceptable acid addition salt thereof to a patient suffering from normal tension glaucoma.

17. The method of claim 16, wherein the pharmaceutically acceptable acid addition salt is dihydrochloride.

18. The method of claim 16, wherein the Lomerizine or a pharmaceutically acceptable acid addition salt is injected intravenously.

* * * * *